US00PP12583P2

(12) United States Plant Patent
Jauchen

(10) Patent No.: US PP12,583 P2
(45) Date of Patent: Apr. 30, 2002

(54) MINIATURE ROSE PLANT NAMED 'KORPIKULA'

(75) Inventor: Daniel E. Jauchen, Santa Barbara, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/556,882

(22) Filed: Apr. 19, 2000

(51) Int. Cl.[7] ..... A01H 5/00
(52) U.S. Cl. ..... Plt./121
(58) Field of Search ..... Plt./121, 116, 120

*Primary Examiner*—Bruce R. Campell
*Assistant Examiner*—June Hwu
(74) *Attorney, Agent, or Firm*—Klarquist Sparkman, LLP

(57) ABSTRACT

Miniature rose plant having a stable, light pink flower color; ease of rooting from cuttings; rapid growth; good pot rose habit; and long shelf life.

1 Drawing Sheet

The present invention relates to a new and distinct variety of rose plant of the miniature class which was discovered as a single branch spontaneous flower color mutation on a rose plant of the variety 'KORfrauma' (U.S. Plant Pat. No. 11,363, filed Mar. 23, 1998) in a greenhouse in Santa Barbara, Calif.

'KORpikula' differs from 'KORfrauma' principally in flower color. 'KORpikula' is a light pink mutation of 'KORfrauma', the flowers of which are a much darker color. Like 'KORfrauma', 'KORpikula' is an ideal pot rose; easy to root from cuttings; grows rapidly; and has a good pot rose habit, long shelf life, and stable flower color.

Asexual reproduction of this new variety by cuttings, as performed at Somis and Santa Barbara, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage: Spontaneous mutation of 'KORfrauma' (U.S. Plant Pat. No. 11,363 filed Mar. 23, 1998).

Classification:

*Botanical.*—*Rosa hybrida.*

*Commercial.*—Miniature rose.

FLOWER

Observations made from specimens six months old grown in a greenhouse environment at Somis and Santa Barbara, Calif., January through November 1999.

Blooming habit: Continuous.

Bud:

*Size.*—¾ inches long when the petals start to unfurl.

*Form.*—The bud form is long; pointed avoid.

*Color.*—When sepals first divide, bud color is Red Group 49C. When half blown, the upper and lower sides of the petals are Red Group 49C.

*Sepals.*—Color: Green Group 138C. Length: ⅞ inch–1 1/16 inch. Shape: Subulate. Surface texture: Covered in fine hairs. There are three normally appendaged sepals. There are two unappendaged sepals with hairy edges.

*Receptacle.*—Color: Green Group 137C. Shape: Funnel. Size: Small (about 7/32 inch×¼ inch). Surface: Smooth.

*Peduncle.*—Length: Short (about 1½ inches). Surface: Prickly; glandular. Color: Green Group 137B. Strength: Stiff; erect.

Bloom:

*Size.*—Small. Average open size is 1½ inches.

*Borne.*—Singly and several together in pyramidal clusters of three to five blooms.

*Stems.*—Strength: Strong. Average length is about 5½ inches.

*Form.*—When first open: High centered. Permanence: Flattens; outer petals curl back.

*Petalage.*—Number of petals under normal conditions: 30 to 35.

*Color.*—The upper and reverse sides of the petals are Red Group 49C. The base of each petal has a small, 3/16 inch×3/16 inch, Green-White Group 157D half moon at the point of attachment The major color on the upper side is Red Group 49C.

*Variegations.*—There is an occasional greenish-white streak at the point of attachment of a petal.

*Discoloration.*—None. Color is stable to petal drop at day 14 to 15.

*Fragrance.*—None.

Petals:

*Texture.*—Thick; leathery.

*Shape.*—Obovate.

*Margin.*—Entire.

*Apex.*—Mucronate.

*Base.*—Obtuse.

*Form.*—Tips slightly recurved.

*Arrangement.*—Imbricated. Petaloids in the center are few (three to seven per flower) and small (⅛ inch to ¼ inch long; 1/16 inch to ⅛ inch wide); same color as petals (Red Group 49C).

*Persistence*.—Petals drop off cleanly before drying.

*Lastingness*.—On the plant: Long (about 14 to 15 days). As a cut flower: Very long (about 18 days).

Reproductive parts:

*Anthers*.—Length: 1/16 inch–3/32 inch. Quantity: Many Color: Yellow-Orange Group 17D. Arrangement: Regular around styles.

*Filaments*.—Color: Yellow Group 12C. Length: 3/16 inch–1/4 inch.

*Pollen*.—Color: Yellow-Orange Group 22A.

*Style*.—Color: Red Group 36D. Length: 3/16 inch–5/16 inch.

*Stigmas*.—Color: Green-White Group 157D.

*Pistils*.—Quantity: 80–100.

*Stamens*.—Quantity: 50–60.

*Hips*.—None observed.

Plant:

*Form*.—Bush.

*Growth*.—Vigorous; upright; branching. At maturity, height is 24 inches, width is 18 inches in a garden setting at Somis, Calif. As a pot rose in a 4 inch pot, height is seven to eight inches and width is five to six inches.

Foliage: Number of leaflets on normal mid-stem leaves: Five.

*Size*.—Small (3½ inches long×2½ inches wide).

*Quantity*.—Abundant.

*Color*.—New foliage: Upper and lower surfaces: Greyed-Orange Group 176B Old foliage: Upper surface: Green Group 137B. Lower surface: Green Group 139C.

Leaflets:

*Shape*.—Pointed oval.

*Texture*.—Smooth on upper surface and smooth with prominent veins on the lower surface.

*Edge*.—Serrated.

*Serration*.—Single; small.

*Petiole rachis*.—Color: Yellow-Green Group 147C.

*Petiole*.—Color: Yellow-Green Group 144B. Texture: Smooth.

*Petiole underside*.—Smooth with occasional prickles.

*Stipules*.—Short (about 1/4 inch); serrated; bearded. Color: Yellow-Green Group 146C. Texture: Smooth.

*Disease resistance*.—Resistant to mildew grown in a greenhouse in 4-inch pots. Not tested for blackspot and rust.

*Pest resistance*.—Not observed.

Wood:

*New wood*.—Color: Green Group 137D. Bark: Smooth.

*Old wood*.—Color: Green Group 137A. Bark: Smooth.

Prickles:

*Quantity*.—On main canes from base: Ordinary. On laterals from main canes: Ordinary.

*Form*.—Short; straight.

*Size*.—1 mm.

*Color when young*.—Greyed-Purple Group 183C.

*Color when mature*.—Greyed-Orange Group 174D.

Small prickles:

*Quantity*.—On main stalks: None. On laterals: None

*Hardiness*.—Plants are hardy to Zone 5.

I claim:

1. A new and distinct variety of rose plant of the miniature class, substantially as herein shown and described, characterized particularly by its stable, light pink flower color; ease of rooting from cuttings; rapid growth; good pot rose habit; and long shelf life.

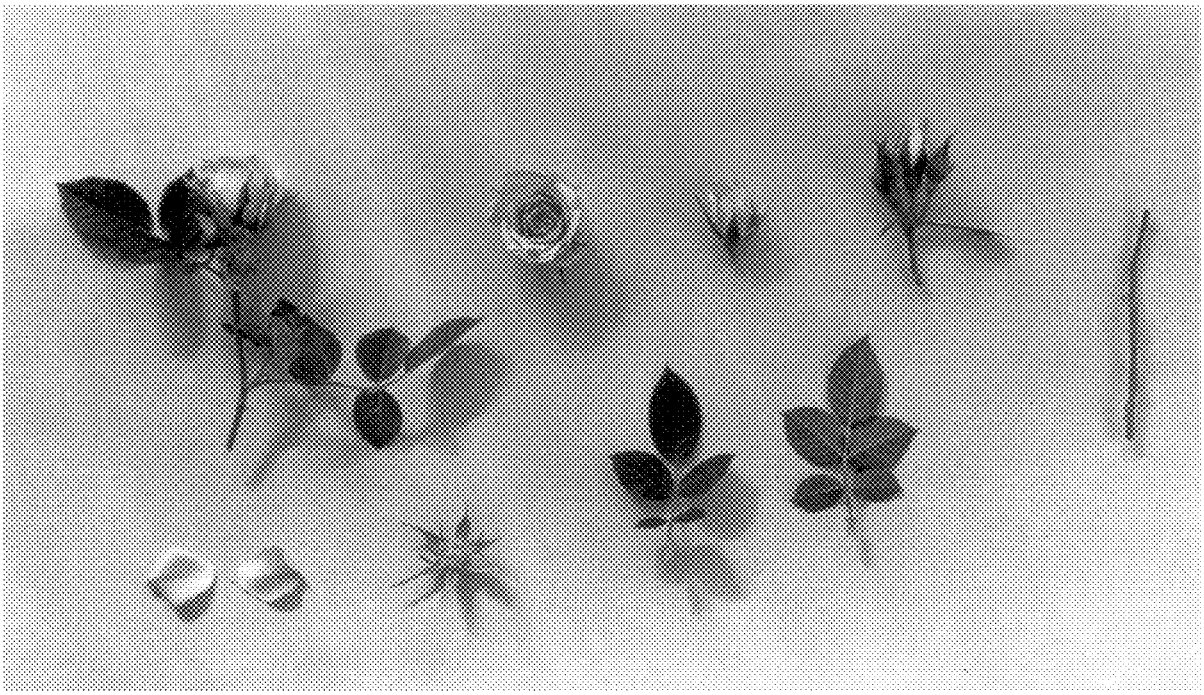

* * * * *